US010022039B2

(12) United States Patent
Schouwink et al.

(10) Patent No.: US 10,022,039 B2
(45) Date of Patent: Jul. 17, 2018

(54) ENDOSCOPE WITH ADJUSTABLE VIEWING DIRECTION

(71) Applicant: OLYMPUS WINTER & IBE GMBH, Hamburg (DE)

(72) Inventors: Peter Schouwink, Hamburg (DE); Takayuki Kato, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 22 days.

(21) Appl. No.: 15/067,480

(22) Filed: Mar. 11, 2016

(65) Prior Publication Data
US 2016/0192831 A1 Jul. 7, 2016

Related U.S. Application Data

(63) Continuation of application No. PCT/EP2014/002359, filed on Sep. 1, 2014.

(30) Foreign Application Priority Data

Sep. 11, 2013 (DE) ........................ 10 2013 218 229

(51) Int. Cl.
A61B 1/00 (2006.01)
A61B 1/05 (2006.01)
(Continued)

(52) U.S. Cl.
CPC ...... *A61B 1/00183* (2013.01); *A61B 1/00096* (2013.01); *A61B 1/00163* (2013.01);
(Continued)

(58) Field of Classification Search
CPC ............ A61B 1/00163; A61B 1/00165; A61B 1/00167; A61B 1/00172; A61B 1/00174;
(Continued)

(56) References Cited

U.S. PATENT DOCUMENTS 3,880,148 A 4/1975 Kanehira et al.
4,140,364 A 2/1979 Yamashita et al.
(Continued)

FOREIGN PATENT DOCUMENTS

CN 102282496 A 12/2011
CN 103229087 A 7/2013
(Continued)

OTHER PUBLICATIONS

International Search Report dated Nov. 10, 2014 issued in PCT/EP2014/002359.

*Primary Examiner* — Ryan Henderson
(74) *Attorney, Agent, or Firm* — Scully, Scott, Murphy & Presser, P.C.

(57) ABSTRACT

An endoscope having an adjustable viewing direction. The endoscope including: an endoscope shaft having a longitudinal axis, a first optical unit disposed in the endoscope shaft, the first optical unit having a first prism pivotable about a pivot axis in order to deflect light, a second optical unit having at least a second prism for deflecting light, which is again deflected by the first prism, the second prism being arranged in a direction parallel to a longitudinal axis of the endoscope shaft, wherein the first prism has a light exit surface facing the second prism, and the second prism has a light admission surface facing towards the light exit surface of the first prism, and a lifting mechanism for lifting the first prism such that upon actuating the lifting mechanism the first prism executes a lifting movement in the direction of the pivot axis.

15 Claims, 4 Drawing Sheets

(51) Int. Cl.
    *G02B 23/24*    (2006.01)
    *G02B 17/04*    (2006.01)
    *G02B 23/02*    (2006.01)

(52) U.S. Cl.
    CPC ...... *A61B 1/00179* (2013.01); *A61B 1/00188* (2013.01); *A61B 1/05* (2013.01); *G02B 17/04* (2013.01); *G02B 23/02* (2013.01); *G02B 23/243* (2013.01); *G02B 23/2423* (2013.01)

(58) Field of Classification Search
    CPC ............ A61B 1/00177; A61B 1/00179; A61B 1/00181; A61B 1/00183; A61B 1/00186; A61B 1/00188; A61B 1/0019; A61B 1/002; A61B 1/00096; A61B 1/04; A61B 1/05; A61B 1/06; A61B 1/07; A61B 1/00193
    See application file for complete search history.

(56) References Cited

U.S. PATENT DOCUMENTS

| | | |
|---|---|---|
| 4,398,811 A | 8/1983 | Nishioka et al. |
| 4,697,577 A | 10/1987 | Forkner |
| 2006/0256450 A1 | 11/2006 | Tesar et al. |
| 2012/0271112 A1 | 10/2012 | Rehe |
| 2013/0044361 A1 | 2/2013 | Katakura |
| 2014/0357952 A1 | 12/2014 | Krohn et al. |

FOREIGN PATENT DOCUMENTS

| | | | |
|---|---|---|---|
| DE | 2347914 A1 | 4/1974 | |
| DE | 2430148 A1 | 1/1975 | |
| DE | 3025186 A1 | 1/1981 | |
| DE | 102010028147 A1 | 10/2011 | |
| DE | 102012202552 B3 | 7/2013 | |
| EP | 2369395 A1 | 9/2011 | |
| JP | WO 2012081349 A1 * | 6/2012 | ......... A61B 1/00183 |
| WO | 2013/124044 A1 | 8/2013 | |

* cited by examiner

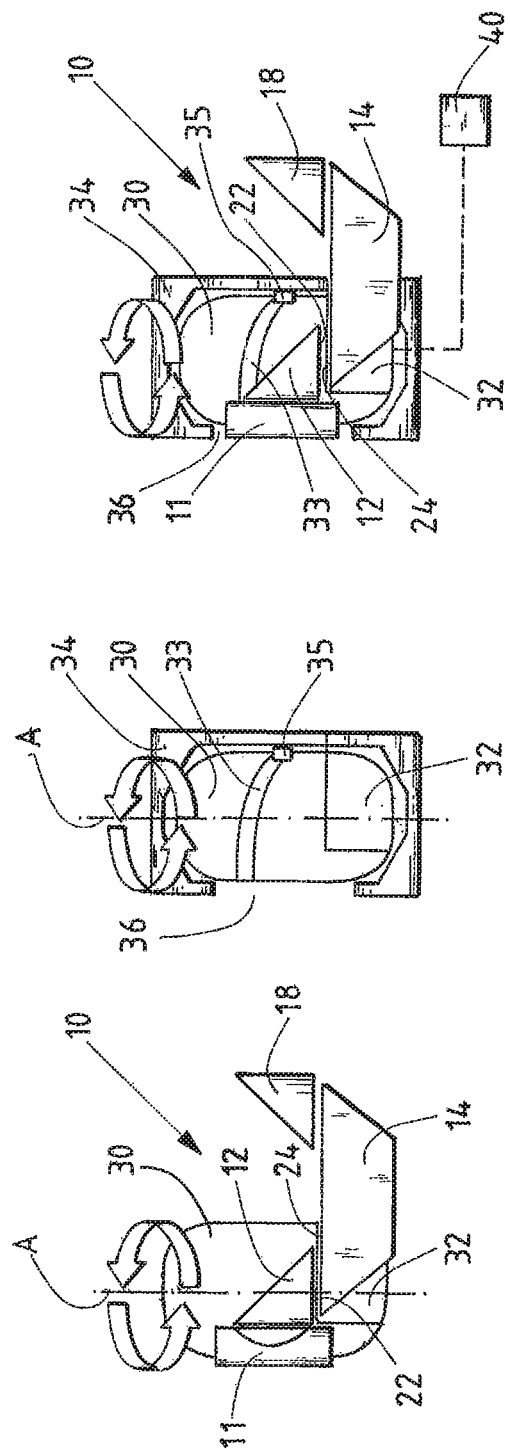

ENDOSCOPE WITH ADJUSTABLE VIEWING DIRECTION

CROSS-REFERENCE TO RELATED APPLICATION

The present application is a continuation of PCT/EP2014/002359 filed on Sep. 1, 2014, which is based upon and claims the benefit to DE 10 2013 218 229.5 filed on Sep. 11, 2013, the entire contents of each of which are incorporated herein by reference.

BACKGROUND

Field

The present application relates to an endoscope, in particular a video endoscope, with an adjustable viewing direction, with an endoscope shaft having a longitudinal axis, wherein in the endoscope shaft a first optical unit, with a prism pivotable about a pivot axis in order to deflect light, is provided and a second optical unit, with at least one fixed prism for deflecting light, which is deflected by the pivotable prism of the first optical unit, is arranged in a direction parallel to the longitudinal axis of the endoscope shaft, wherein the pivotable, prism, which can be a distal prism, has a light exit surface facing towards the prism, which can be a proximal prism, of the second optical unit, and the prism of the second optical unit has a light admission surface facing towards the light exit surface of the pivotable prism, such as by being oriented in parallel.

Prior Art

Endoscopes, and in particular video endoscopes, in which the light of an operative field entering a distal tip of an endoscope shaft of the endoscope is directed through an optical system onto one or more image sensors, are known in different designs. Thus, there are endoscopes with a straight-ahead view, a so-called 0° viewing direction, or endoscopes with a lateral viewing direction, which have for example a lateral viewing direction of 30°, 45°, 70° or the like deviating from the 0° viewing direction. In this context, the degree numbers indicate the angle between the central viewing axis and the longitudinal axis of the endoscope shaft. Further, there are endoscopes or respectively video endoscopes with an adjustable lateral viewing direction, in which the viewing angle, i.e. the deviation from the straight-ahead view, is adjustable.

When adjusting the viewing angle, the deviation from the straight-ahead view, in particular in relation to the longitudinal axis of the endoscope shaft, is thus changed.

EP 2 369 395 A1 further shows an optical system for a video endoscope in which a change in the viewing angle occurs such that a prism of a prism unit with three prisms is turned about a rotary axis which lies perpendicular or respectively transverse to the longitudinal axis of the endoscope shaft. The two other prisms, which define the optical light path together with the first prism, are not rotated so that the reflection surface of the first prism, which is turned, is twisted with respect to the corresponding reflection surface of the second prism.

Another endoscope with variable viewing direction is described in DE 10 2010 028 147 A1.

Reference will now be made to FIGS. 1-3 from DE 10 2012 202 552 A1 disclosing a video endoscope of the prior art. FIG. 1 shows a schematic perspective representation of a video endoscope 1 with a proximal handle 2 and a rigid endoscope shaft 3. A viewing window 5 is arranged on the distal tip 4 of the endoscope shaft 3, behind which a distal section 6 of the endoscope shaft 3 is arranged, which has a prism unit (not shown) and an image sensor unit (not shown).

The viewing window 5 on the distal tip 4 is designed curved and asymmetrical. In particular, the viewing window 5 is designed spherically curved in one design. The viewing window 5 is thus designed to support a variable lateral viewing angle. A change in the viewing direction, i.e. a change in the azimuth angle about the longitudinal axis of the endoscope shaft 3, is effectuated by a turning of the handle 2 about the central axis of rotation or respectively longitudinal axis of the endoscope shaft 3. The jacket tube of the endoscope shaft 3 is connected with the handle. The prism unit (not shown) on the distal tip 4 also rotates with the turning of the handle 2.

The handle 2 has a first control element designed as a rotary wheel 7 and a second control element designed as a sliding switch 8.

For retaining the horizontal position of the displayed image, the rotary wheel 7 is held tight while turning the handle 2. This causes the image sensor inside the endoscope shaft 3 to not make the movement.

The sliding switch 8 is moved in order to change the viewing angle, i.e. the deviation of the viewing direction from the straight-ahead view. A sliding of the sliding switch 8 distally leads for example to an enlargement of the viewing angle; a retraction of the sliding switch 8 proximally effectuates in this case a reduction in the viewing angle up to the straight-ahead view. The actuation of the sliding switch 8 involves a turning of the image sensor in order to retain the horizontal position of the displayed image even in the case of a twisting of the prism unit against each other.

FIG. 2 shows a corresponding prism unit 10 according to the state of the art schematically from the side. On the left side of the image, light from a central light path 21, which is shown as a dashed-and-dotted line, enters through a viewing window 5 of the endoscope shaft and enters a first, distal prism 12 of the prism unit 10 through a negative meniscus lens 11 designed as an admission lens. The light hits the mirrored surface 13 of the prism 12 and is reflected downward in the direction of a second prism 14 of the prism unit 10 as well as a mirrored surface 15 of the second prisms 14.

The mirrored surface 15 of the prism 14 has an acute angle to the bottom side 17 of the second prism 14 so that the central light path is first reflected onto a central section of the bottom side 17, which is also mirrored, and from there to a second mirrored surface 16 of the second prism 14. This second mirrored surface 16 also has an acute angle to the bottom side 17, so that the central light path is, in turn, reflected upwards (axis B). There, the light enters a third prism 18 of the prism unit 10 with a mirrored surface 19, through which the light of the central light path 21 is in turn reflected centrally in a direction parallel to the longitudinal axis of the endoscope shaft 3 and exits the prism unit 10 through an exit lens 20.

Moreover, another part of an optical fiber bundle 25 is shown above the prism unit 10, by means of which light is directed from the proximal to the distal tip in order to illuminate an otherwise unilluminated operative field.

The first prism 12 of the prism unit 10 is turned or respectively pivoted about the perpendicular axis A, which is also called the pivot axis, in order to adjust the lateral viewing angle. The mirrored surface 13 of the first prism 12 and the mirrored surface 15 of the fixed prism 14 of the prism unit 10 are thereby also rotated against each other so that the horizontal position of the image, which is forwarded proximally, is changed during a turning of the first pivotable prism 12 about the axis A. This must be counterbalanced by a turning of the image sensor or the image sensors. FIG. 3 shows the prism unit 10 from FIG. 2 in a schematic top view. The first prism 12 is arranged in a 0° viewing direction. The first prism 12 is pivotably mounted about the pivot axis A together with the negative meniscus lens 11. In this case, the overlapping area is twisted between the mirrored surfaces 13 of the first prism 12 and 15 of the second prism 14. A turning of the horizon, which will be explained below, takes place in the case of a rotary or respectively pivoting movement of the first prism 12.

SUMMARY

Based on this state of the art, an object is to provide an endoscope with adjustable viewing direction, in which a capturing of examined objects is enabled in a simple manner during a viewing angle adjustment and a focusing of the captured object images can be improved for different viewing angle settings.

Such object can be solved by an endoscope, such as video endoscope, with an adjustable viewing direction, with an endoscope shaft having a longitudinal axis, wherein in the endoscope shaft a first optical unit, with a prism pivotable about a pivot axis in order to deflect light, is provided and a second optical unit, with at least one fixed prism for deflecting light, which is deflected by the first pivotable prism of the first optical unit, is arranged in a direction parallel to the longitudinal axis of the endoscope shaft, wherein the pivotable prism, which can be the distal prism, has a light exit surface facing towards the prism, which can be the proximal prism, of the second optical unit, and the prism of the second optical unit has a light admission surface facing towards the light exit surface, which can be oriented in parallel, of the pivotable prism, which is developed in that a lifting mechanism is provided for the pivotable prism in such a way that upon actuating the lifting mechanism the pivotable prism executes a lifting movement in the direction of the pivot axis or respectively, when the lifting mechanism is actuated, a lifting movement of the pivotable prism is executed in the direction of the pivot axis.

The exemplary embodiments are based on the idea that, during the pivoting process of the distal pivotable prism of a prism unit, the focus or respectively the focusing plane is changed or respectively adjusted by a lifting movement of the pivotable prism, wherein the focus is also adjusted accordingly before or during or after the pivoting of the pivotable prism with respect to the fixed prism of the prism unit as a result of the position change in the direction of the pivot axis during a change in the viewing direction. The lifting movement of the pivotable prism takes place in the direction of the pivot axis. The lifting movement can be executed before or after the pivoting of the prism using the lifting mechanism provided for it. The lifting movement and the pivoting movement of the pivotable prism can be executed simultaneously.

The focusing of the light beams entering the prisms of a prism unit can be improved during a viewing direction adjustment of the pivotable prism such that a better image of the captured viewing area can be achieved during the capturing of the light beams by use of an image sensor.

The first optical unit and the second optical unit are thereby components of a prism unit, wherein the prism unit can consist of three prisms. The prism unit can have a pivotable prism and two fixed prisms. The prism unit itself can be arranged in a movable manner in the endoscope shaft so that the prism unit is rotatable, such as about the longitudinal axis of the endoscope shaft.

It is provided in one embodiment that the lifting mechanism is configured as a lifting pivoting mechanism, wherein the lifting pivoting mechanism is set up for the pivotable prism in such a way that, upon actuating the lifting pivoting mechanism the pivotable prism is pivoted about the pivot axis and, simultaneously, a lifting movement of the pivotable prism can be executed in the direction of the pivot axis. A lifting movement of the pivotable prism in the direction of the pivot axis hereby overlies the pivoting movement of the pivotable prism.

Furthermore, the pivotable prism can execute a continuous lifting movement during a pivoting movement, which can be continuous, by means of or during actuation of the lifting pivoting mechanism. In particular, the lifting pivoting mechanism can be actuatable from a proximal handle of the video endoscope. When using the video endoscope, the pivotable prism of the prism unit or respectively of the first optical unit in the endoscope shaft is pivoted accordingly about the pivot axis through a manual actuation, wherein the pivotable prism is simultaneously moved towards the fixed prism or respectively away from the fixed prism. Since the pivoting movements of the pivotable prism can be configured in a reversible manner, a lifting movement of the pivotable prism with respect to the fixed prism can be executed during a viewing angle adjustment.

In the case of arrangement of the pivotable prism with a viewing direction of 0° to the longitudinal axis of the endoscope shaft, the distance between the light exit surface of the pivotable prism and the light admission surface of the fixed prism is maximal and/or that, in the case of arrangement of the pivotable prism with a viewing direction of 90° to the longitudinal axis of the endoscope shaft, the distance between the light exit surface of the pivotable prism and the light admission surface of the fixed prism can be minimal.

The first optical unit of the prism unit can have the pivotable prism and at least one negative meniscus lens, wherein the pivotable prism has a light admission side and the at least one negative meniscus lens is arranged on the light admission side of the pivotable prism.

Moreover, in the case of the video endoscope, the first optical unit, which can have the pivotable prism and/or with the at least one negative meniscus lens for the pivotable prism can be arranged in a sleeve, wherein the sleeve is pivotably mounted. In particular, the sleeve is in this case can be arranged pivotably in the endoscope shaft, wherein the sleeve is movable in the direction of the pivot axis of the pivotable prism so that when orienting the lifting mechanism as well as the lifting pivoting mechanism, the sleeve and the pivotable prism arranged in it execute a lifting movement.

The sleeve for the first optical unit can be arranged in a housing, which can be fixed, such as by being fixed with respect to the sleeve for the pivotable prism.

Moreover, the sleeve for the first optical unit can have a guide groove facing towards the housing on the outside in the form of a lifting guideway and the housing surrounding the sleeve can have a pin engaging in the guide groove of the sleeve.

The housing can have a guide groove on the inside facing towards the sleeve for the first optical unit in the form of a lifting guideway and the sleeve surrounded by the housing can have a pin engaging in the guide groove of the housing.

Moreover, the second optical unit of the prism unit can have another prism, which can be fixed, wherein the other prism has a light admission surface facing towards the first fixed prism of the second optical unit and the first fixed prism of the second optical unit has a light exit surface facing towards the light admission surface of the other prism, which can be oriented in parallel, wherein the distance between the light exit surface of the first fixed prism and of the light admission surface of the other fixed prism is constant.

Further characteristics will become evident from the description of the embodiments together with the claims and the included drawings. Embodiments can fulfill individual characteristics or a combination of several characteristics.

BRIEF DESCRIPTION OF THE DRAWINGS

The embodiments are described below, without restricting the general idea of the invention, based on exemplary embodiments in reference to the drawings, whereby we expressly refer to the drawings with regard to the disclosure of all details that are not explained in greater dew tail in the text.

FIG. 5a schematically illustrates a side view of a prism unit with a pivotable prism arranged in a sleeve.

FIG. 5b schematically illustrates a cross-section through a sleeve for a pivotable prism with a housing surrounding the sleeve.

FIG. 5c schematically illustrates a side view in cross-section through a prism unit with a pivotable prism arranged in a sleeve.

In the drawings, the same or similar elements and/or parts are provided with the same reference numbers in order to prevent the item from needing to be reintroduced.

DETAILED DESCRIPTION

Figure 1:
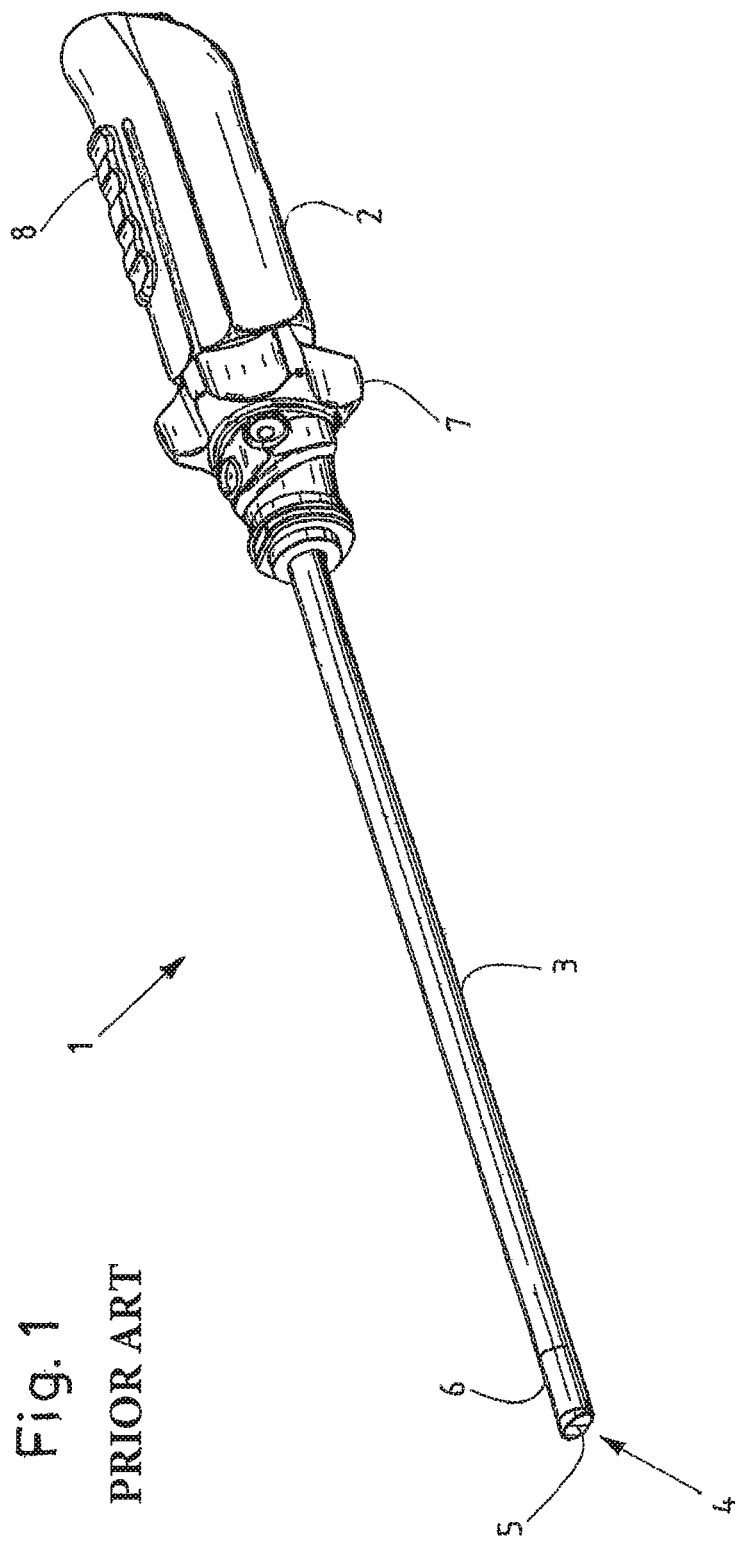
FIG. 1 illustrates a schematic perspective representation of a video endoscope of the prior art.
Figure 2:
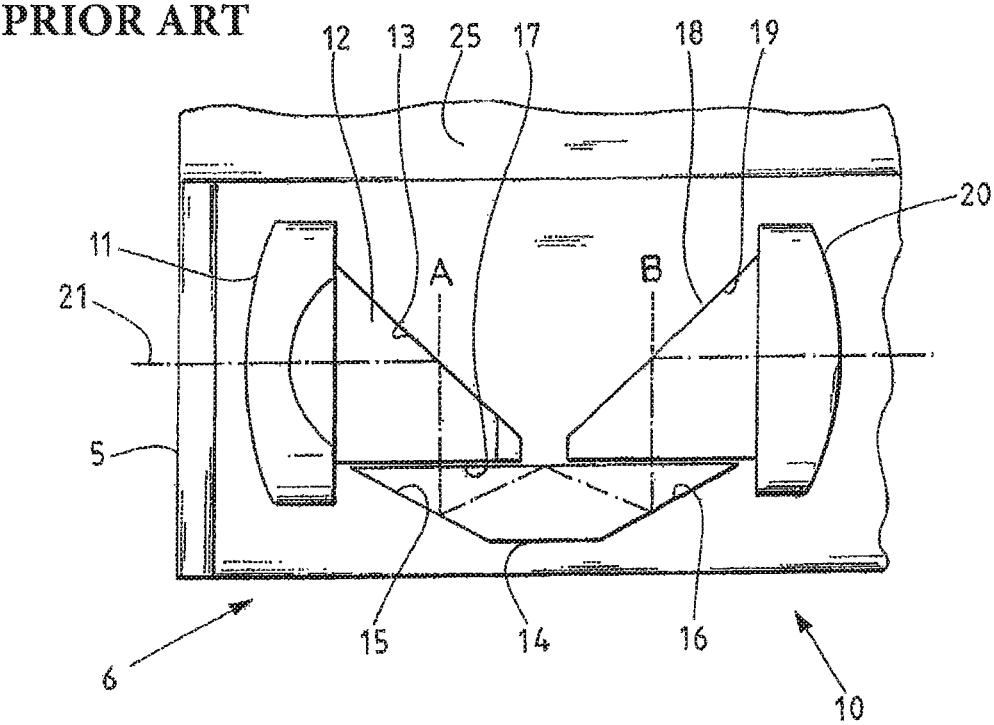
FIG. 2 illustrates a schematic side view of a prism unit according to the prior art.
Figure 3:
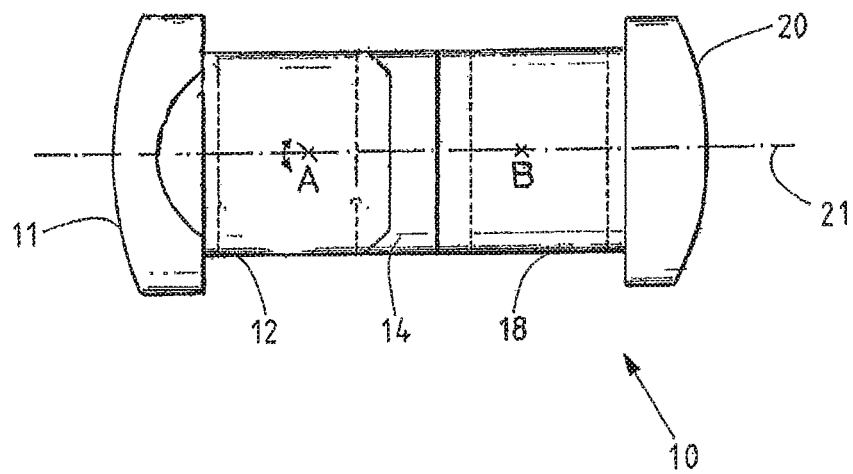
FIG. 3 illustrates a schematic top view of the prism unit in FIG. 2.
Figure 4A:
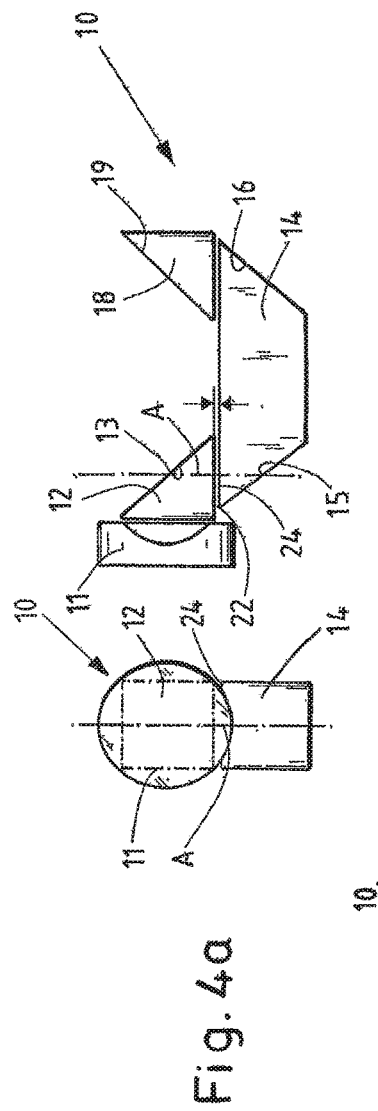
FIGS. 4a, 4b, 4c schematically illustrate respectively a front view in the right representation and a side view in the left representation of a prism unit for a video endoscope, wherein the images each show different positions of the pivoted prism.
Figure 4B:
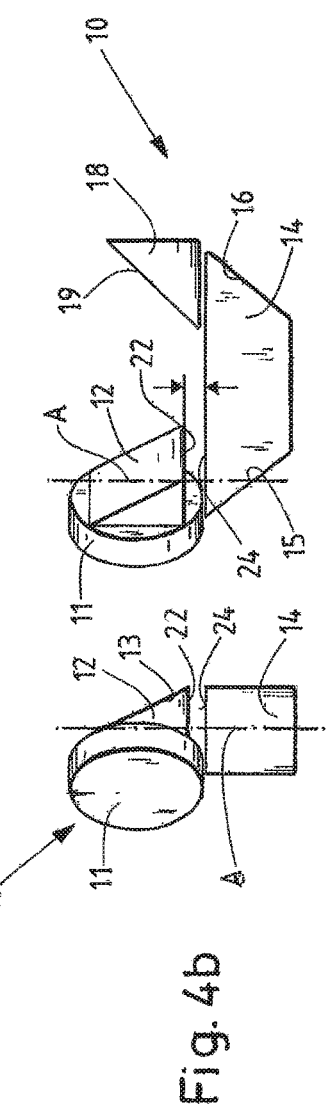
Figure 4C:
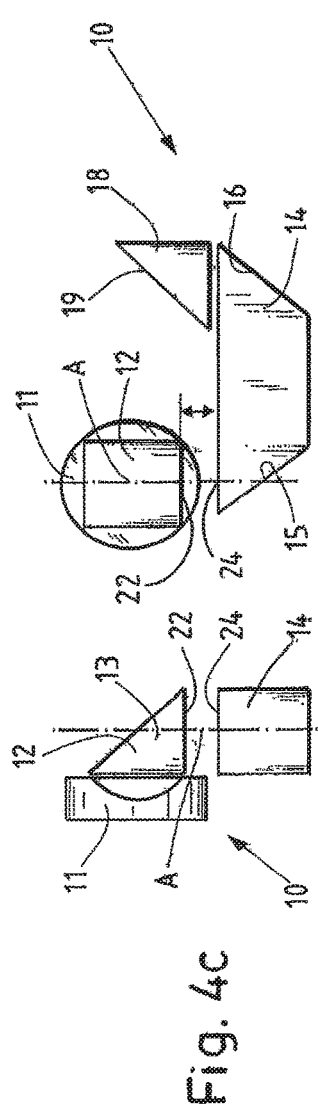

Referring now to FIGS. 4a to 4c, each schematically illustrating a front view and a side view of a prism unit 10, wherein the left area of the figures shows the front view of the prism unit 10 and the right area the respective associated side view of the prism unit.

The prism 12 of the prism unit 10 is pivotably mounted about the axis A so that the first prism 12 is pivoted about the perpendicular axis A in order to adjust the lateral viewing angle. Prism 14 and prism 18 are in this context designed fixed in the prism unit 10 with respect to the first prism 12.

In the position of prism 12 shown in FIG. 4a, it is arranged in the 0° viewing direction. The second prism 14 has a light admission side 24, which is arranged opposite a light exit side 22 of the first prism 12. The light exit side 22 of the first prism 12 and the light admission side 24 of the second prism 14 are aligned and arranged parallel to each other.

When changing the viewing direction by turning the first prism 12 about the axis A, the distance between the light exit side 22 of the prism 12 and of the light admission side 24 of the prism 14 is changed or respectively increased. FIG. 4b shows the position of the prism 12 when turned 45°, i.e. in a viewing direction with 45°. It can be seen in this context that the distance between the light exit side 22 of the prism 12 and the light admission side 24 of the prism 14 is increased with respect to the 0° viewing direction (compare with FIG. 4a).

FIG. 4c shows the position of the prism 12 with a 90° viewing direction, wherein, in this position, the distance between the light exit surface 22 of the prism 12 and the light admission surface 24 of the prism 14 is the greatest. When pivoting the prism 12 back about the pivot axis A into the 0° viewing direction (compare with FIG. 4a), the distance between the light exit surface 22 of the prism 12 and the parallel-aligned light admission surface 24 of the prism 12 changes continuously. In the case of a 0° viewing direction, the distance between the light exit surface 22 of the prism 12 and the light admission surface 24 of the second prism 14 is minimal. The maximum distance between the light exit surface 22 of the prism 12 and of the light admission surface 24 of the prism 14 is at a maximum in the 90° viewing direction. Between the two viewing directions 0° and 90°, the distance between the light exit surface 22 and the light admission surface 24 changes continuously when the prism 12 is pivoted, whereby the focus is accordingly adjusted or respectively changed simultaneously with the change in distance between the prism 12 and the prism 14.

As can be seen in FIGS. 4a to 4c, the negative meniscus lens 11 arranged on the prism 12 is pivoted together with the prism 12. In order to execute the pivoting movement of the first prism 12, a pivoting mechanism (not shown here) or respectively a corresponding lifting pivoting mechanism is provided in the endoscope. When the lifting pivoting mechanism is actuated, the viewing direction of the first prism 12 is changed, wherein the prism 12 executes a lifting movement in the direction of the first axis A simultaneously during the pivoting movement of the prism 12 with respect to the fixed prism 14, whereby the distance between the light exit surface 22 of the prism 12 and the light admission surface 24 of the second prism 14 changes continuously.

FIG. 5a shows schematically in a side view the prism unit 10, wherein the first prism 12 together with the meniscus lens 11 arranged on the prism 12 is arranged in a receiving device 30 configured as a sleeve. The receiving device 30 is pivotable together with the prism 12 and the meniscus lens 11 about the axis A in the endoscope shaft (not shown here).

The receiving device 30 for the meniscus lens 11 and the prism 12 arranged in it has a corresponding outlet for the meniscus lens 11 or respectively for the light admission side of the prism 12. Furthermore, the sleeve-like receiving device 30 has on one side or respectively on the bottom side a recess 32, in which the prism 14 with its light admission side 24 is arranged. The receiving device 30 is pivotable or respectively rotatably mounted about the axis A with respect to the fixed second prism 14 of the prism unit 10 as well as the other fixed prism 18 of the prism unit.

FIG. 5b shows schematically in cross-section the arrangement of the receiving device 30 (without prism 12 and meniscus lens 11) in a housing 34 in cross-section. The receiving device 30 is pivotably mounted within the housing 34, wherein the housing 34 has an opening 36 in the pivot area of the prism 12 or respectively of the negative meniscus lens 11 arranged on the prism 12. The receiving device 30 has on the outside a guide groove 33 designed in the circumferential direction of the receiving device 30. The guide groove 33 is curved according to the type of a lifting guideway. The receiving device 30 is mounted in the housing 34 such that the receiving device 30 together with the prism 12 and the meniscus lens 11 executes a lifting movement along the axis A during the turning of the receiving device 30 with respect to the housing 34 arranged in the endoscope shaft.

In order to execute the lifting movement in direction A, a pin body 35, which engages in the guide groove 33 of the receiving device 30, is arranged inside the housing 34.

FIG. 5c shows schematically the prism unit 10 together with the receiving device 30 and the housing 34 for the receiving device 30. In order to pivot the pivotable prism 12 together with the receiving device 30 in the housing 34 and simultaneously execute a lifting movement in the direction of the axis A, a correspondingly actuatable actuator 40 is connected for example in the handle of an endoscope so that, upon actuation of the schematically sketched actuator 40 designed as a lifting pivoting mechanism, a pivoting and lifting movement of the prism 12 is executed about the axis A or respectively in the direction of axis A.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE LIST

1 Video endoscope
2 Handle
3 Endoscope shaft
4 Distal tip
5 Viewing window
6 Distal section
7 Rotary wheel
8 Sliding switch
9 Jacket tube
10 Prism unit
11 Meniscus lens
12 First prism
13 Mirrored surface
14 Second prism
15, 16 Mirrored surface
17 Bottom side
18 Third prism
19 Mirrored surface
20 Exit lens
21 Central light path
22 Light admission side
24 Light exit side
25 Optical fiber bundle
30 Receiving device
32 Recess
33 Guide groove
34 Housing
35 Pin body
36 Opening
40 Actuator

What is claimed is:
1. An endoscope having an adjustable viewing direction, the endoscope comprising:
an endoscope shaft having a longitudinal axis,
a first optical unit disposed in the endoscope shaft, the first optical unit having a first prism pivotable about a pivot axis in order to deflect light,
a second optical unit having at least a second prism for deflecting light, which is further deflected by the first prism of the first optical unit, the second prism being arranged in a direction parallel to a longitudinal axis of the endoscope shaft, wherein the first prism has a light exit surface facing the second prism of the second optical unit, and the second prism of the second optical unit has a light admission surface facing towards the light exit surface of the first prism, the light exit surface of the first prism being parallel to the light admission surface of the second prism, and
a mechanism for lifting the first prism such that the first prism moves along the pivot axis as a result of a rotation of the first prism about the pivot axis, the mechanism comprising:
a first body having a cam; and
a second body rotatable relative to the first body, the second body having a cam surface, the cam and cam surface being configured such that relative rotation between the first body and the second body moves the first prism along the pivot axis;
wherein rotation of the first prism changes a distance between the light exit surface of the first prism and the light admission surface of the second prism.

2. The endoscope according to claim 1, wherein the first prism is distal to the second prism.

3. The endoscope according to claim 1, wherein the mechanism is configured to simultaneously pivot the first prism about the pivot axis and move the first prism along the pivot axis.

4. The endoscope according to claim 1, wherein the first prism is continuously moved along the pivot axis upon rotation of the first prism.

5. The endoscope according to claim 1, wherein, when the first prism is arranged in a viewing direction of 0° to the longitudinal axis of the endoscope shaft, the distance between the light exit surface of the first prism and the light admission surface of the second prism is at a maximum.

6. The endoscope according to claim 1, wherein, when the first prism is arranged in a viewing direction of 90° to the longitudinal axis of the endoscope shaft, the distance between the light exit surface of the first prism and the light admission surface of the second prism is at a minimum.

7. The endoscope according to claim 1, wherein the first optical unit further comprises at least one negative meniscus lens, wherein the first prism has a light admission side and the one negative meniscus lens is arranged on the light admission side of the first prism.

8. The endoscope according to claim 1, wherein the second body is a sleeve, wherein the first optical unit is arranged in the sleeve, wherein the sleeve is pivotably mounted in the endoscope shaft.

9. The endoscope according to claim 8, wherein the first body is a housing, wherein the sleeve is arranged in the housing.

10. The endoscope of claim 9, wherein the housing is fixed relative to the sleeve.

11. The endoscope according to claim 9, wherein the cam surface is a guide groove on an exterior surface of the sleeve, the guide groove facing towards the housing and the cam of the housing is a pin engaging in the guide groove of the sleeve.

12. The endoscope according to claim 1, wherein the second optical unit has a third prism, wherein the third prism has a light admission surface facing towards the second prism of the second optical unit and the second prism of the second optical unit has a light exit surface facing towards the light admission surface of the third prism, wherein a distance between the light exit surface of the second prism and the light admission surface of the third prism is constant.

13. The endoscope according to claim 12, wherein the third prism is fixed relative to the second prism.

14. The endoscope according to claim 12, wherein the light exit surface of the second prism is oriented in parallel to the light admission surface of the third prism.

15. A video endoscope having an adjustable viewing direction, the endoscope comprising:
- an endoscope shaft having a longitudinal axis,
- a first optical unit disposed in the endoscope shaft, the first optical unit having a first prism pivotable about a pivot axis in order to deflect light,
- a second optical unit having at least a second prism for deflecting light, which is further deflected by the first prism of the first optical unit, the second prism being arranged in a direction parallel to a longitudinal axis of the endoscope shaft, wherein the first prism has a light exit surface facing the second prism of the second optical unit, and the second prism of the second optical unit has a light admission surface facing towards the light exit surface of the first prism, the light exit surface of the first prism being parallel to the light admission surface of the second prism,
- a mechanism for lifting the first prism such that the first prism moves along the pivot axis as a result of a rotation of the first prism about the pivot axis; and
- an image sensor in optical communication with the second optical unit;

wherein rotation of the first prism changes a distance between the light exit surface of the first prism and the light admission surface of the second prism; and the mechanism comprising:
- a first body having a cam; and
- a second body rotatable relative to the first body, the second body having a cam surface, the cam and cam surface being configured such that relative rotation between the first body and the second body moves the first prism along the pivot axis.

\* \* \* \* \*